(12) United States Patent
Soundararajan et al.

(10) Patent No.: US 7,105,677 B2
(45) Date of Patent: Sep. 12, 2006

(54) PROCESSES FOR THE PREPARATION OF ANTIVIRAL 7-AZAINDOLE DERIVATIVES

(75) Inventors: Nachimuthu Soundararajan, Kendall Park, NJ (US); Serge Benoit, Laval (CA); Stephane Gingres, Montreal (CA)

(73) Assignee: Bristol-Myers Squibb Company, Princeton, NJ (US)

( * ) Notice: Subject to any disclaimer, the term of this patent is extended or adjusted under 35 U.S.C. 154(b) by 111 days.

(21) Appl. No.: 10/948,405

(22) Filed: Sep. 23, 2004

(65) Prior Publication Data

US 2005/0059695 A1 Mar. 17, 2005

Related U.S. Application Data

(62) Division of application No. 10/395,320, filed on Mar. 24, 2003, now Pat. No. 6,884,889.

(60) Provisional application No. 60/367,401, filed on Mar. 25, 2002.

(51) Int. Cl.
*C07D 471/04* (2006.01)
(52) U.S. Cl. .................................. 546/113
(58) Field of Classification Search ................ 546/113
See application file for complete search history.

(56) References Cited

U.S. PATENT DOCUMENTS 6,476,034 B1 11/2002 Wang et al.

FOREIGN PATENT DOCUMENTS

WO WO 99/12918 3/1999
WO WO 00/76527 12/2000

OTHER PUBLICATIONS

Pederson et al., Antiviral Chem. Chemother., 1999, 10, 285-314.
Mahadevan et al., J. Heterocycl. Chem., 1992, 29, 359-367.
Hands et al., Synthesis, 1996, 877-882.
Dobson et al., Synth. Commun., 1991, 21, 611-617.
Sakamoto et al., Chem. Pharm. Bull., 1987, 35, 1823-1828.
Schneller et al., J. Org. Chem., 1980, 45, 4045-4048.
Desai et al., Org. Prep. Proceed. Intl., 1976, 8 85-86.
Adamczyk et al., Org. Prep. Proceed. Intl., 1996, 28, 470-474.
Rossen et al., Tetrahedron Lett., 1995, 36, 6419-6422.
Wang et al., J. Org. Chem., 1999, 64, 7661-7662.
Wang et al., J. Org. Chem., 2000, 65, 4740-4742.
Girgis et al. J. of Het. Chem., vol. 26, p. 317-325, 1989.
Feiser and Feiser, Advanced Organic Chemistry, Reinholf Pub. Co., p. 285, 1961.

*Primary Examiner*—Bernard Dentz
(74) *Attorney, Agent, or Firm*—Deanna L. Baxam

(57) ABSTRACT

Provided are processes and synthetic intermediates useful for the preparation of azaindole piperazine diamide derivatives of the formula

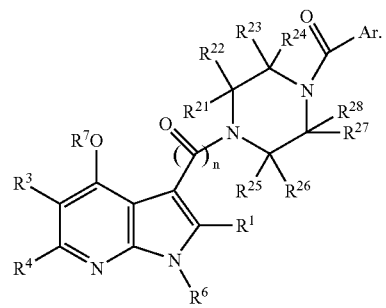

These azaindole piperazine diamide derivatives, among other things, are useful as therapeutic agents for the treatment of HIV and AIDS.

26 Claims, No Drawings

PROCESSES FOR THE PREPARATION OF ANTIVIRAL 7-AZAINDOLE DERIVATIVES

This application claims a benefit of priority from U.S. Provisional Application No. 60/367,401, the entire disclosure of which is herein incorporated by reference.

The present invention relates to processes for the preparation of certain 7-azaindole compounds. More particularly the invention relates to azaindole piperazine diamide derivatives that possess antiviral activity. In addition, the invention relates to certain substituted azaindole synthetic intermediates useful for, among other things, the preparation of agents for the treatment of HIV and AIDS.

One useful therapeutic approach for the treatment of HIV and AIDS utilizes antiviral agents that target and inhibit HIV-1 reverse transcriptase. Often these reverse transcriptase inhibitors are administered to patients in combination with antiviral agents that target other viral proteins, such as HIV protease. Non-nucleoside reverse transcriptase inhibitors (NNRTIs) have recently gained an increasingly important role in the therapy of HIV infections (Pederson et al., *Antiviral Chem. Chemother.* 1999, 10, 285–314).

One of the more effective classes of these non-nucleoside inhibitors are azaindole derivatives which are disclosed in copending U.S. patent application Ser. No. 09/912,710, filed Jul. 25, 2001. Among the azaindoles disclosed in the application are certain 4-alkoxy-7-azaindoles that have an (N-aroylpiperazin-N'-yl)oxoacetyl moiety at the 3-position. For example, the compound, (R)-N-(benzoyl)-3-methyl-N'-[(4-methoxy-7-azaindol-3-yl)-oxoacetyl]-piperazine 7a is an effective reverse transcriptase inhibitor and antiviral agent of this class.

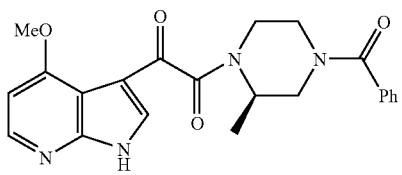

7a

Syntheses of 7a and related analogs have been described in copending U.S. patent application Ser. No. 09/912,710. In procedures described therein for the preparation of N-(aroyl)-N'-[(4-alkoxy-7-azaindol-3-yl)-oxoacetyl]-piperazines, the peripheral substituents on the heterocycle are typically introduced by addition of the oxoacetyl substituent to the 3-position of the heterocyclic nucleus, followed by introduction of the alkoxy substituent to the 4-position. While these procedures are suitable for the preparation of working quantities of these 7-azaindole analogs, alternative synthetic procedures for the preparation of N-(aroyl)-N'-[(4-alkoxy-7-azaindol-3-yl)-oxoacetyl]-piperazines more amenable to scale-up are desirable.

SUMMARY OF THE INVENTION

In one embodiment, the invention relates to a process for the preparation of a compound of the formula

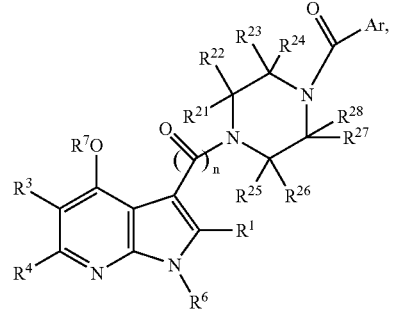

7 wherein $R^1$, $R^3$ and $R^4$ are each independently selected from the group consisting of H, $C_1$–$C_6$ alkyl, $C_3$–$C_6$ cycloalkyl, $C_2$–$C_6$ alkenyl, $C_4$–$C_6$ cycloalkenyl, $C_2$–$C_6$ alkynyl, halogen, cyano, phenyl, $C(O)R^5$, $C(O)NR^8R^9$, $OR^{10}$, $SR^{11}$, and $NR^{12}R^{13}$;

$R^5$ is selected from the group consisting of H, $C_1$–$C_6$ alkyl, $C_3$–$C_6$ cycloalkyl, $C_2$–$C_6$ alkenyl, and $C_4$–$C_6$ cycloalkenyl;

$R^8$ and $R^9$ are each independently selected from the group consisting of $C_1$–$C_6$ alkyl, $C_3$–$C_6$ cycloalkyl, $C_3$–$C_6$ alkenyl, $C_4$–$C_6$ cycloalkenyl and $C_3$–$C_6$ alkynyl; provided the carbon atoms which comprise the carbon-carbon double bond of said $C_3$–$C_6$ alkenyl or the carbon-carbon triple bond of said $C_3$–$C_6$ alkynyl are not the point of attachment to the nitrogen to which $R^8$ or $R^9$ is attached;

$R^{10}$ and $R^{11}$ are each independently selected from the group consisting of $C_1$–$C_6$ alkyl, $C_1$–$C_6$ alkyl substituted with one to three halogen atoms, $C_3$–$C_6$ cycloalkyl, $C_2$–$C_6$ alkenyl, $C_4$–$C_6$ cycloalkenyl and $C_3$–$C_6$ alkynyl; provided the carbon atoms which comprise said carbon-carbon triple bond of said $C_3$–$C_6$ alkynyl are not the point of attachment to the oxygen or sulfur to which $R^{10}$ or $R^{11}$ is attached;

$R^{12}$ and $R^{13}$ are each independently selected from the group consisting of $C_1$–$C_6$ alkyl, $C_3$–$C_6$ cycloalkyl, $C_3$–$C_6$ alkenyl, $C_4$–$C_6$ cycloalkenyl and $C_3$–$C_6$ alkynyl; and $C(O)R^{14}$; provided the carbon atoms which comprise the carbon-carbon double bond of said $C_3$–$C_6$ alkenyl, $C_4$–$C_6$ cycloalkenyl or the carbon-carbon triple bond of said $C_3$–$C_6$ alkynyl are not the point of attachment to the nitrogen to which $R^{12}$ or $R^{13}$ is attached;

$R^{14}$ is selected from the group consisting of H, $C_1$–$C_6$ alkyl, $C_3$–$C_6$ cycloalkyl, $C_2$–$C_6$ alkenyl, $C_4$–$C_6$ cycloalkenyl and $C_2$–$C_6$ alkynyl;

$R^6$ is selected from the group consisting of H, $C_1$–$C_6$ alkyl, $C_3$–$C_6$ cycloalkyl, $C_4$–$C_6$ cycloalkenyl, $C(O)NR^{16}R^{17}$, benzyl, $C_3$–$C_6$ alkenyl and $C_3$–$C_6$ alkynyl; provided the carbon atoms which comprise the carbon-carbon double bond of said $C_3$–$C_6$ alkenyl or the carbon-carbon triple bond of said $C_3$–$C_6$ alkynyl are not the point of attachment to the nitrogen to which $R^6$ is attached;

$R^{16}$ and $R^{17}$ are each independently selected from the group consisting of H, $C_1$–$C_6$ alkyl, $C_3$–$C_6$ cycloalkyl, $C_3$–$C_6$ alkenyl, $C_5$–$C_6$ cycloalkenyl and $C_3$–$C_6$ alkynyl; provided the carbon atoms which comprise the carbon-carbon double bond of said $C_3$–$C_6$ alkenyl, $C_5$–$C_6$ cycloalkenyl or the carbon-carbon triple bond of the $C_3$–$C_6$ alkynyl are not the point of attachment to the nitrogen to which $R^{16}$ and $R^{17}$ are attached;

$R^7$ is selected from the group consisting of $CH_3$, $CH_2CH_3$, $CH_2CF_3$ and $CH_2CH_2CH_3$;

$R^{21}$, $R^{22}$, $R^{23}$, $R^{24}$, $R^{25}$, $R^{26}$, $R^{27}$ and $R^{28}$ are each independently selected from the group consisting of H, $C_1$–$C_6$ alkyl, $C_3$–$C_6$ cycloalkyl, $C_2$–$C_6$ alkenyl, $C_4$–$C_6$ cycloalkenyl, $C_2$–$C_6$ alkynyl, $CR^{29}R^{30}OR^{31}$, $C(O)R^{32}$, $CR^{33}(OR^{34})OR^{35}$, $CR^{36}NR^{37}R^{38}$, $C(O)OR^{39}$, $C(O)NR^{40}R^{41}$, $CR^{42}R^{43}F$, $CR^{44}F_2$, and $CF_3$;

$R^{29}$, $R^{30}$ $R^{31}$, $R^{32}$, $R^{33}$, $R^{36}$, $R^{42}$, $R^{43}$ and $R^{44}$ are each independently selected from the group consisting of H, $C_1$–$C_6$ alkyl, $C_3$–$C_6$ cycloalkyl, $C_2$–$C_6$ alkenyl, $C_4$–$C_6$ cycloalkenyl, $C_2$–$C_6$ alkynyl and $C(O)R^{45}$;

$R^{34}$, $R^{35}$ and $R^{39}$ are each independently selected from the group consisting of H, $C_1$–$C_6$ alkyl, $C_3$–$C_6$ cycloalkyl, $C_3$–$C_6$ alkenyl, $C_4$–$C_6$ cycloalkenyl, and $C_3$–$C_6$ alkynyl; provided the carbon atoms which comprise the carbon-carbon triple bond of said $C_3$–$C_6$ alkynyl are not the point of attachment to the oxygen to which $R^{35}$ and $R^{39}$ are attached;

$R^{37}$ and $R^{38}$ are each independently selected from the group consisting of H, $C_1$–$C_6$ alkyl, $C_3$–$C_6$ cycloalkyl, $C_3$–$C_6$ alkenyl, $C_4$–$C_6$ cycloalkenyl and $C_3$–$C_6$ alkynyl; provided the carbon atoms which comprise the carbon-carbon triple bond of said $C_3$–$C_6$ alkynyl are not the point of attachment to the nitrogen to which $R^{37}$ and $R^{38}$ are attached;

$R^{40}$ and $R^{41}$ are each independently selected from the group consisting of H, $C_1$–$C_6$ alkyl, $C_3$–$C_6$ cycloalkyl, $C_2$–$C_6$ alkenyl, $C_4$–$C_6$ cycloalkenyl and $C_3$–$C_6$ alkynyl; provided the carbon atoms which comprise the carbon-carbon triple bond of said $C_3$–$C_6$ alkynyl are not the point of attachment to the nitrogen to which $R^{40}$ and $R^{41}$ are attached;

$R^{45}$ is selected from the group consisting of H, $C_1$–$C_6$ alkyl, $C_3$–$C_6$ cycloalkyl, $C_2$–$C_6$ alkenyl, $C_4$–$C_6$ cycloalkenyl, and $C_2$–$C_6$ alkynyl;

Ar is selected from the group consisting of

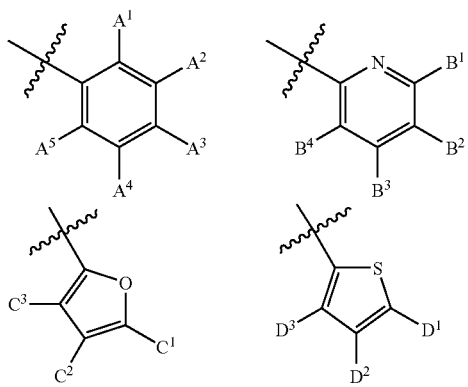

$A^1$, $A^2$, $A^3$, $A^4$, $A^5$, $B^1$, $B^2$, $B^3$, $B^4$, $C^1$, $C^2$, $C^3$, $D^1$, $D^2$ and $D^3$ are each selected from the group consisting of H, cyano, halogen, nitro, $C_1$–$C_6$ alkyl, $C_3$–$C_6$ cycloalkyl, $C_2$–$C_6$ alkenyl, $C_4$–$C_6$ cycloalkenyl, $C_2$–$C_6$ alkynyl, $OR^{46}$, $NR^{47}R^{48}$, $SR^{49}$, $N_3$ and $CH(-N=N-)-CF_3$;

$R^{46}$ is selected from the group consisting of H, $C_1$–$C_6$ alkyl, $C_3$–$C_6$ cycloalkyl, $C_2$–$C_6$ alkenyl, $C_4$–$C_6$ cycloalkenyl, $C_2$–$C_6$ alkynyl; provided the carbon atoms which comprise the carbon-carbon triple bond of said $C_2$–$C_6$ alkynyl are not the point of attachment to the nitrogen to which $R^{46}$ is attached;

$R^{47}$ and $R^{48}$ are each independently selected from the group consisting of H, $C_1$–$C_6$ alkyl, $C_3$–$C_6$ cycloalkyl, $C_3$–$C_6$ alkenyl, $C_5$–$C_6$ cycloalkenyl, $C_3$–$C_6$ alkynyl, and $C(O)R^{51}$; provided the carbon atoms which comprise the carbon-carbon double bond of said $C_5$–$C_6$ alkenyl, $C_4$–$C_6$ cycloalkenyl, or the carbon-carbon triple bond of said $C_3$–$C_6$ alkynyl are not the point of attachment to the nitrogen to which $R^{47}$ and $R^{48}$ are attached;

$R^{49}$ is selected from the group consisting of H, $C_1$–$C_6$ alkyl, $C_3$–$C_6$ cycloalkyl, $C_2$–$C_6$ alkenyl, $C_4$–$C_6$ cycloalkenyl, $C_3$–$C_6$ alkynyl and $C(O)R^{50}$; provided the carbon atoms which comprise the carbon-carbon triple bond of said $C_3$–$C_6$ alkynyl are not the point of attachment to the sulfur to which $R^{47}$ is attached;

$R^{50}$ is $C_1$–$C_6$ alkyl or $C_3$–$C_6$ cycloalkyl; and $R^{51}$ is selected from the group consisting of H, $C_1$–$C_6$ alkyl and $C_3$–$C_6$ cycloalkyl. The process includes the steps of:

(a) treating a compound of the formula

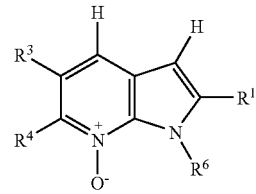

2 with a chlorinating agent selected from one of
(i) a compound of the formula $R^aSO_2Cl$ 

wherein $R^a$ is $C_1$–$C_4$ alkyl; trifluoromethyl; phenyl or naphthalene, which phenyl or napthalene can be substituted with one or more H, $C_1$–$C_6$ alkyl, $C_3$–$C_6$ cycloalkyl, $C_2$–$C_6$ alkenyl, $C_4$–$C_6$ cycloalkenyl, $C_2$–$C_6$ alkynyl, halogen, cyano, nitro, phenyl, $C(O)R^5$, $C(O)NR^8R^9$, $OR^{10}$;

(ii) a compound of the formula $R^bCOCl$ 

wherein $R^b$ is $C_1$–$C_4$ alkyl; trihalomethyl; $C(O)R^5$; phenyl or naphthalene, which phenyl or naphthalene can be substituted with one or more H, $C_1$–$C_6$ alkyl, $C_3$–$C_6$ cycloalkyl, $C_2$–$C_6$ alkenyl, $C_4$–$C_6$ cycloalkenyl, $C_2$–$C_6$ alkynyl, halogen, cyano, nitro, phenyl, $C(O)R^5$, $C(O)NR^8R^9$, $OR^{10}$; or (iii) a compound of the formula

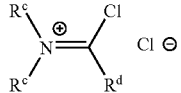

wherein $R^c$ is independently H, $C_1$–$C_4$ alkyl; trifluoromethyl; phenyl or naphthalene, which naphthalene is substituted with one or more H, $C_1$–$C_6$ alkyl, $C_3$–$C_6$ cycloalkyl, $C_2$–$C_6$ alkenyl, $C_4$–$C_6$ cycloalkenyl, $C_2$–$C_6$ alkynyl, halogen, cyano, phenyl and $OR^{10}$; and wherein $R^d$ is H, $C_1$–$C_4$ alkyl; halogen; trifluoromethyl; phenyl or naphthalene, which naphthalene is substituted with one or more H, $C_1$–$C_6$ alkyl, $C_3$–$C_6$ cycloalkyl, $C_2$–$C_6$ alkenyl, $C_4$–$C_6$ cycloalkenyl, $C_2$–$C_6$ alkynyl, halogen, cyano, phenyl and $OR^{10}$; to give a compound of the formula

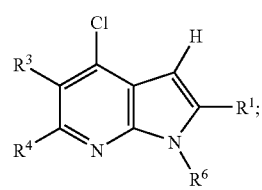

3

(b) reacting the compound of the formula 3 with a potassium alkoxide of the formula $R^7O-K+$. 

to give a compound of the formula

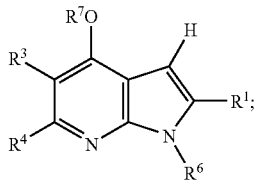

4

(c) treating the compound of the formula 4 with a compound of the formula

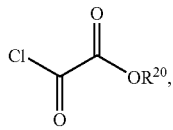

9 wherein $R^{20}$ is $C_1$–$C_6$ alkyl, $C_3$–$C_6$ cycloalkyl, aryl $[C_1$–$C_6]$alkyl or aryl in the presence of a Lewis acid to give a compound of the formula

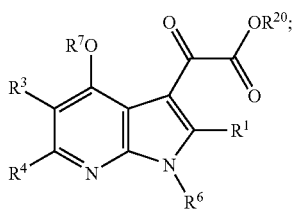

5

(d) hydrolyzing the ester of the compound of the formula 5 to give a compound of the formula

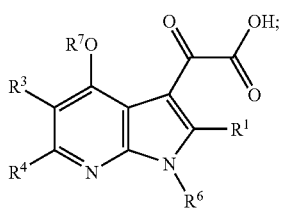

6 and (e) coupling the compound of the formula 6 with a compound of the formula

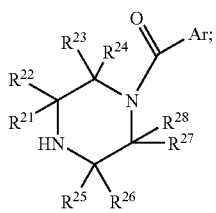

8 using an acyl activating reagent to give the compound of the formula 7.

In preferred embodiments of the process for preparing the compound of the formula 7, $R^7$ is $CH_3O$. In a particularly preferred embodiment of this process $R^1$, $R^3$, $R^4$ and $R^6$ are H.

In another embodiment, the invention relates to a process for preparing a compound of the formula

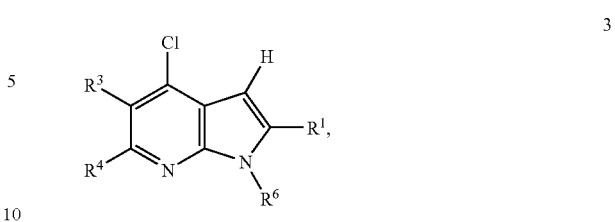

3 wherein $R^1$, $R^3$, $R^4$ and $R^6$ are as described above, by chlorinating a compound of the formula

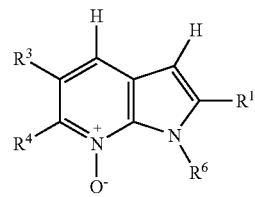

2 using one of the three chlorinating agents described above, i.e., a sulfonyl chloride reagent of the formula $R^aSO_2Cl$, a chlorinating agent of the formula $R^bCOCl$, or a compound of the formula

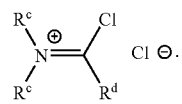

In a preferred embodiment for preparing the compound of the formula 3, $R^1$ and $R^3$ are H; $R^4$ is H, halogen or cyano (with H being particularly preferred); and $R^6$ is H, methyl or allyl (with H being particularly preferred).

In another embodiment, the invention relates to a process for preparing a compound of the formula

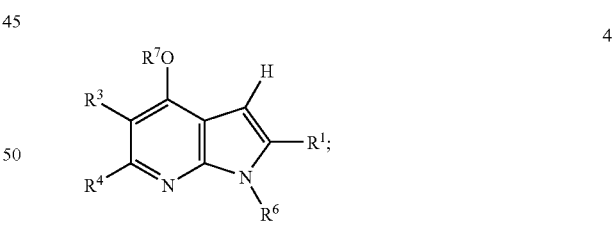

4 by treating a compound of the formula 3 with a potassium alkoxide of the formula $R^7O$—K+.

In preferred embodiments of the process for preparing the compound of the formula 4, $R^1$ is H or $C_1$–$C_3$ alkyl; $R^3$ is H; $R^4$ is H, halogen, cyano or $C(O)R^5$ (wherein $R^5$ is as described above); and $R^6$ is H, $C_1$–$C_3$ alkyl, allyl or benzyl. In a particularly preferred embodiment of this process $R^3$, $R^4$ and $R^6$ are H.

In another embodiment, the invention relates to a process for preparing a compound of the formula

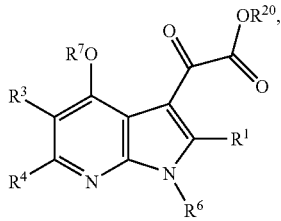

wherein $R^1$, $R^3$, $R^4$, $R^6$, $R^7$ and $R^{20}$ are as described above, by treating a compound of the formula 4, with a chlorooxoacetate reagent of the formula

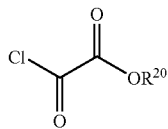

in the presence of a Lewis acid. Preferably $R^{20}$ is methyl.

In another aspect, the invention relates to certain compounds that are useful, among other things, for preparing the compound of the formula 7. For example, the compounds of the formulas

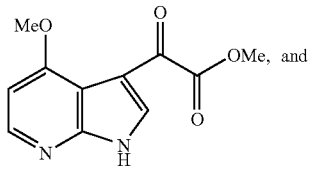

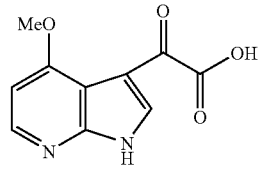

are useful synthetic intermediates.

DETAILED DESCRIPTION OF THE INVENTION

In accordance with the invention, a compound of the formula 7, wherein $R^1$, $R^3$, $R^4$ and $R^6$ are as described above can be obtained by the synthetic sequence depicted in Scheme 1. In the sequence, the compound of the formula 1 is initially elaborated to incorporate alkoxy substituents at the 4-position of the heterocycle to provide the compound of the formula 4. The 4-alkoxy substituent is introduced by way of pyridine N-oxide formation, regioselective chlorination of the 4-position, and nucleophilic displacement of the resultant chloride by an alkoxide. Next, an electrophilic acylation of the 3-position yields a glyoxylate ester intermediate, the compound of the formula 5. Hydrolysis of the ester and activation of the resultant carboxylic acid, yields an activated carboxylic acid intermediate. The intermediate is then coupled with an aroyl piperazine of the formula 8 to provide the compound of the formula 7. The ring positions specified herein may be referenced according to the following nomenclature:

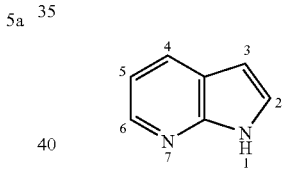

Scheme 1

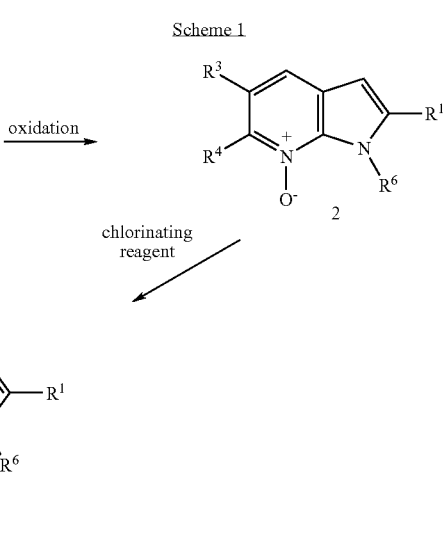

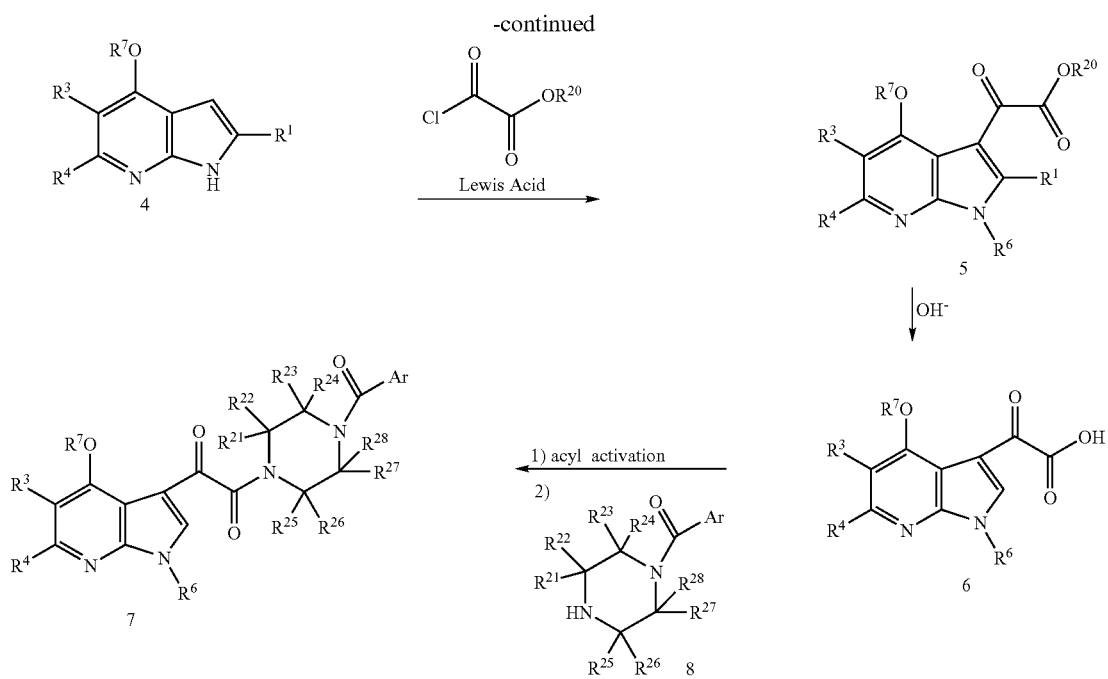

While 7-azaindole, per se, is available from commercial sources, (Aldrich Chemical Co., Milwaukee, Wis.) other starting 7-azaindoles can be prepared by methods described in the literature (Mahadevan et al. *J. Heterocycl. Chem.*, 1992, 29, 359–367) or Hands et al. *Synthesis* 1996, 866–882). These references and similar references show some examples of the preparation of substituted 7-azaindole compounds. It will be apparent to those of skill in the art that the general methodology can be extended to azaindoles that have different substituents in the starting materials. Azaindoles are also prepared via the routes described in copending U.S. patent application Ser. No. 09/912,710, herein incorporated by reference in its entirety. Some of these routes are summarized in Schemes 2 and 3 (below), and in the accompanying discussion.

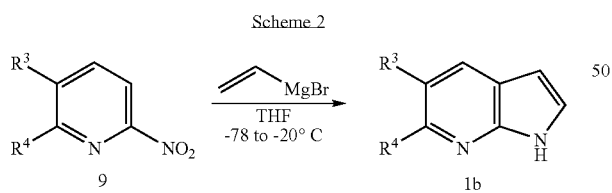

In Scheme 2, the Bartoli indole synthesis (Dobson et al. *Synth. Commun.* 1991, 21, 611–617) is extended to prepare substituted 7-azaindoles. Nitropyridine 9 is reacted with an excess of vinyl magnesium bromide at −78° C. After warming up to −20° C., the reaction provides the desired 7-azaindole 1b. Generally these temperature ranges are effective but in specific examples can be varied usually by no more than about 20° C. but occasionally by more in order to optimize the yield. The vinyl magnesium bromide can be obtained commercially as a solution in tetrahydrofuran or sometimes more optimally can be prepared fresh from vinyl bromide and magnesium using literature procedures that are well known in the art.

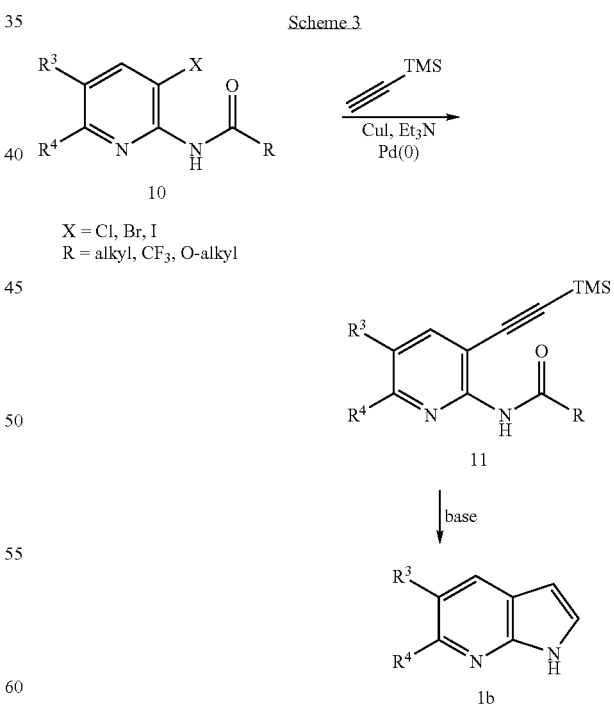

In Scheme 3 (above), trimethylsilylacetylene is coupled onto a halo-pyridine 10 using a Pd(0) catalyst to furnish 10. Subsequent treatment with base effects cyclization of 11 to afford 7-azaindole 1b (Sakamoto et al. *Chem. Pharm. Bull.*

1987, 35, 1823–1828). Suitable bases for the second step include sodium methoxide or other sodium, lithium or potassium alkoxide bases.

The compound of the formula 1 wherein $R^6$ is alkyl can be prepared by deprotonation of N-1 of the compound 1b, and alkylation of the resulting anion with suitable alkyl halides, e.g., chlorides, bromides or iodides, preferably bromides or iodides. In an analogous manner, the compound of the formula 1 wherein $R^6$ is cycloalkyl, cycloalkenyl, alkenyl or alkynyl can be prepared by reaction of the anion of the compound of the formula 1b with the corresponding halides. Skilled chemists will recognize that mesylates, tosylates and the like can be used in place of halides as alkylating agents. The deprotonation of the 7-azaindole 1b can be conducted using a strong base, e.g., alkali metal hydride, in an inert organic solvent, e.g., tetrahydrofuran, dimethylformamide, at temperatures from about –78 to about 100° C.

In the process, the chloro compound of the formula 3 can be obtained from the compound of the formula 1, via the N-oxide intermediate 2. As will be recognized by those of ordinary skill in the art, oxidation of the pyridine N-atom serves to render the 4-position of the heterocyclic nucleus susceptible to nucleophilic addition. The oxidation of the compound of the formula 1 is conducted using an oxidizing agent such as a peracid, e.g., peracetic acid, meta-chloroperoxybenzoic acid (mCPBA), or hydrogen peroxide. Other oxidation reagents that could be used for the pyridine N-oxide formation include hydrogen peroxide-urea reagent, magnesium monoperoxyphthalate hexahydrate, and potassium peroxymonosulfate (Oxone®). Generally, the oxidation is conducted in a polar organic solvent such as acetone, DMF or ethyl acetate at temperatures of about –5 to 35° C., preferably at about room temperature.

In preferred embodiments the oxidation is conducted using a peracid, more preferably using mCPBA in ethyl acetate. The oxidation with mCPBA is typically performed using from about 1 to 3 equivalents of mCPBA, preferably about 1.05–1.4 equivalents. The product from the mCPBA treatment is typically isolated as the meta-chlorobenzoic (mCBA) acid addition salt. Treatment of the salt with aqueous base, e.g., aqueous potassium carbonate liberates the free base 2 for use in the next synthetic step.

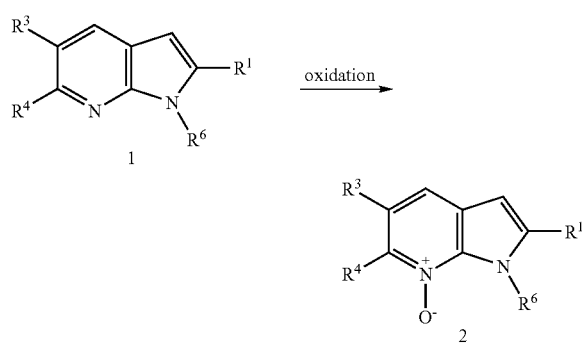

The compound of the formula 3, is obtained from the compound of formula 2 by treatment with a chlorinating agent. The chlorinating reagent is preferably one of: an alkyl/arylsulfonyl chloride of the formula $R^aSO_2Cl$; an alkyl/aryl carboxylic acid chloride of the formula $R^bCOCl$; or a chloromethylene N,N-disubstituted ammonium chloride of the formula

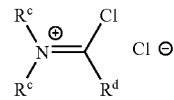

wherein $R^a$, $R^b$, $R^c$ and $R^d$ are as described above. Applicants have found that the use of these preferred chlorinating reagents provides the compound of the formula 3 with improved regioselectivity relative to conventional chlorination procedures for 7-azaindoles. For example, treatment of the compound of the formula of the 2a with phosphorus oxychloride using a procedures similar to that described by Schneller et. al. in *J. Org. Chem.* 1980, 45, 4045–4048 led to mixtures of the desired 4-chloro isomer 2a and the 3-chloro isomer 12. For example, when the chlorination was conducted in toluene at 90 to 95° C., then ratios of the 4-chloro isomer/3-chloro isomer ranged from 3:1 to 9:1 (Scheme 4). Due to the less desirable product mixture in the crude product, multiple recrystallizations were used to obtain the product with acceptable isomeric purity (i.e., greater than 99:1). The multiple recrystallizations of the product resulted in a lower overall yields of the purified product. Chlorination procedures that provide improved regioselectivity are therefore preferable from the standpoint of both operational simplicity and improved overall yield.

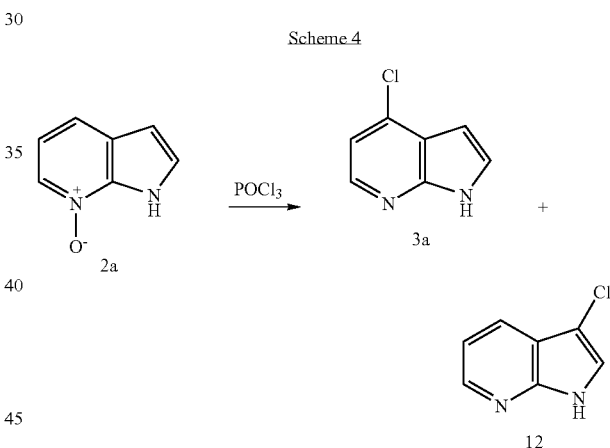

Scheme 4

In preferred embodiments the chlorination of 2 is conducted with an alkyl or arylsulfonyl chloride of the formula $R^aSO_2Cl$. Preferably $R^a$ is methyl, phenyl or p-methylphenyl. More preferably $R^a$ is methyl. There is generally about 2 to 3 equivalents of the sulfonyl chloride reagent present per mole of compound of the formula 2. Preferably however, at least 2.58 equivalents of the sulfonyl chloride reagent is used to achieve convenient reaction rates, with a range of 2.58–2.75 equivalents being particularly preferred.

The chlorination reaction is typically conducted in a polar aprotic solvent such as dichloromethane, 2-methyltetrahydrofuran, butyl acetate, N,N-dimethylacetamide, N-methylpyrrolidone, acetonitrile, toluene, or DMF. Preferably the solvent for the reaction is acetonitrile or DMF, with DMF being particularly preferred. Generally, the concentration of compound 2 in the reaction solvent is from about 1 to 2 M, with a preferred concentration of 1.25 to 1.33 M.

The reaction can be conducted at temperatures of about 45 to 90° C., with preferred temperatures of about 50 to 75° C.

While the reaction can be carried out at higher temperatures, lower temperature are preferred for improved regioselectivity.

The compound of the formula 4 can be formed by nucleophilic displacement of the chloro group with a potassium alkoxide of the formula

wherein $R^7$ is $CH_3$, $CH_2CH_3$, $CH_2CF_3$ or $CH_2CH_2CH_3$. The alkoxide can be generated by adding potassium metal to a solution of the parent alcohol. Alternatively the potassium alkoxide can be prepared by treatment of a solution of the parent alcohol with a strong potassium base, e.g., potassium hydride, hexamethyldisilazide, diisopropylamide. In some cases, e.g., potassium methoxide and ethoxide, the potassium alkoxide are commercially available. In a preferred process, potassium methoxide is used.

In one preferred embodiment of the process, the alkoxide displacement is conducted in a slurry of a carbocyclic aromatic solvent and portions of diatomaceous earth (e.g., Celite®). Both the compound of the formula 3 and potassium alkoxide have limited solubility in the reaction solvent. While not being bound by theory, Applicants believe that the diatomaceous earth acts as a phase transfer reagent that provides surface areas where the reaction can take place. In any case, improved conversions are observed for process runs containing portions of diatomaceous earth. In contrast, in trials where diatomaceous earth was omitted from the reaction mixtures, the mixtures contained a gummy residue that was insoluble in the carbocyclic aromatic solvent, and poor conversions of compound of the formula 3, were observed.

Generally the alkoxide displacement in this preferred embodiment, is conducted at temperatures of from about 105 to 120° C., with preferred temperatures of from about 105 to 110° C. Typically there are at least 2 equivalents of the potassium alkoxide added per molar equivalent of 3. Preferably, from 2 to 5 equivalents of potassium alkoxide are used in the process.

Preferred carbocyclic aromatic solvents for this alkoxide displacement step include toluene, xylene and mesitylene, with toluene being particularly preferred. Generally, from about 15 to 40 mL, preferably from about 18.5 to 30 mL of toluene is added per gram of the compound of the formula 3. In addition, from about 1 to 2 g, preferably from about 1–1.5 g of diatomaceous earth is added per gram of the compound of the formula 3.

In another preferred embodiment of the process, the alkoxide displacement is conducted without any added diatomaceous earth. In this displacement process, the compound of the formula 3 is treated with both a potassium alkoxide of the formula

and a lithium alkoxide of the formula

in a mixture of a carbocyclic aromatic solvent and t-butanol. Both the inclusion of lithium alkoxide and the cosolvent t-butanol improve the solubility of the alkoxide in the reaction solvent to achieve practical reaction rates and conversions. As this preferred process does not require a filtration step to remove the diatomaceous earth during reaction workup, this process is particularly preferred for larger scale processes where filtration steps are less convenient to implement.

In this diatomaceous earth-free embodiment, the carbocyclic aromatic solvent is preferably xylene. The concentration of the compound of the formula 3 in the reaction is preferably less than 1.0 M, more preferably between 0.8 to 1.0 M. As the reaction mixture is typically a slurry, higher concentrations of 3 in the reaction lead to mixtures that are too thick for efficient stirring.

Preferred embodiments of the diatomaceous earth-free embodiment process utilize potassium methoxide in the displacement step. Typically, the reaction is conducted with about 2 to about 5 equivalents of potassium methoxide, preferably about 2.2 to 4 equivalents per mole of 3. In addition, there is typically about 1 to 2 equivalents, preferably about 1.5 to 2 equivalents, of lithium methoxide per mole of 3. The process is generally conducted at 110 to 125° C. with preferred temperatures of 114 to 117° C.

The compound of the formula 5

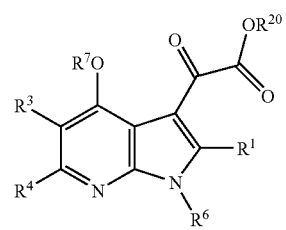

can be prepared by adding a chlorooxoacetate reagent of the formula

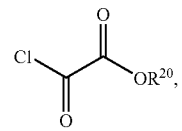

wherein $R^{20}$ is an alkyl, cycloalkyl, arylalkyl or aryl group, to the compound of the formula 4 in the presence of a Lewis Acid.

The crude product from this addition reaction may contain small amounts (e.g., less than 20%) of a diacylated product with a glyoxylate group at the the N-1 position in addition to the glyoxylate group at C-3. The presence of the diacylated material in the reaction product generally requires no further purification steps, as the N-1 glyoxylate group is cleaved under the basic conditions used to hydrolyze the ester of the glyoxylate group at the C-3 position.

A number of Lewis acids can be used for the glyoxylate addition reaction including aluminum trichloride, tin (IV) chloride, ferric chloride and zirconium tetrachloride. Preferably, the Lewis acid used in this glyoxylate addition reaction is aluminum trichloride. Typically, there is at least 4 equivalents of aluminum trichloride used per mole of the compound of the formula 4. Preferably, the reaction is performed using 4 to 5 equivalents of aluminum trichloride per mole of the compound of the formula 4.

The glyoxylate addition is preferably conducted in a solvent mixture of dichloromethane and a [$C_1$–$C_3$]nitroalkane (e.g., nitromethane, nitropropane) at temperatures of about 0 to 20° C. While the addition will take place in a neat solution of the nitroalkane, due to safety concerns, a diluted solvent mixture of the nitroalkane and dichloromethane is preferred. Preferably the solvent mixture comprises a nitroalkane and dichloromethane in a ratio of 4:1 to 17:3. A preferred nitroalkane solvent is nitromethane.

The glyoxylate ester moiety at the 3-position of the compound of the formula 5 is subsequently hydrolyzed to give the carboxylic acid of the formula 6.

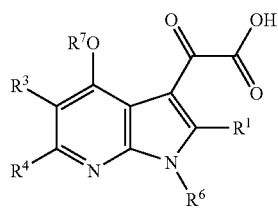

The hydrolysis can be conducted using an aqueous base, e.g., sodium or potassium hydroxide, at temperatures of about 10 to 30° C. The carboxylic acid of the formula 6, is preferably isolated as the free acid after acidic workup. If higher purities are desired, the carboxylic acid of the formula 6 can be further purified by recrystallization from suitable solvents such as dimethylsulfoxide and water.

As will be apparent to those of ordinary skill in the art, in some embodiments of the process, the glyoxylate ester moiety of the formula 5 may be susceptible to alternative cleavage conditions, such as acidic or reductive conditions. For example, acidic condition can be used to hydrolyze the ester in embodiments of the compound of the formula 5, wherein the glyoxylate ester is a t-butyl ester.

The compound of the formula 7

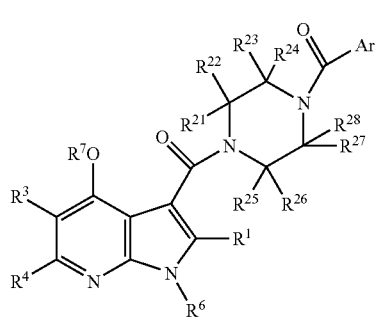

can then be prepared by coupling the carboxylic acid of the formula 6 with an aroyl piperazine of the formula 8,

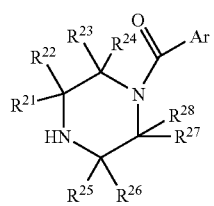

wherein $R^{21}$–$R^{28}$ and Ar are as described above, using an acyl activating agent. Acyl activating agents include reagents effective to prepare an acid chloride intermediate such as (chloromethylene)-N,N-dimethylammonium chloride (Vilsmeier reagent) or oxalyl chloride. Acyl activating agents also include reagents effective to prepare activated ester intermediates such as (3-diethoxyphosphoryloxy)-1,2,3-benzotriazin-4(3H)-one (DEPBT). Coupling procedures utilizing DEPBT and acyl amides are described in copending U.S. patent application Ser. No. 09/912,710.

The aroyl piperazine of the formula 8 can be prepared according to well established procedures such as those described by Desai et al. (*Org. Prep. Proced. Intl.* 1976, 8, 85–86), Adamczyk et al. (*Org. Prep. Proced. Intl.* 1996, 28, 470–474), Rossen et al. (*Tetrahedron Lett.* 1995, 36, 6419–6422) and Wang et al. (*J. Org. Chem.* 1999, 64, 7661–7662 and *J. Org. Chem.* 2000, 65, 4740–4742). Other examples for the preparation of aroyl piperazines are described in WO 00/765271, herein incorporated by reference. For example, (R)-2-methyl-4-benzoyl piperazine amide 8a

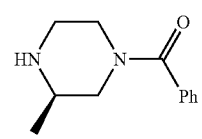

can be prepared by treatment of (R)-2-methylpiperazine 13 (commercially available from Aldrich Chemical Company, Milwaukee, Wis.)

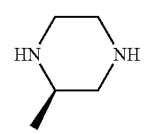

with an equimolar amount of methyl benzoate and dimethylaluminum chloride at room temperature.

The following examples further illustrate the present invention, but of course, should not be construed as in any way limiting its scope.

EXAMPLE 1

Preparation of 1H-Pyrrolo[2,3-b]pyridine 1-oxide 2a

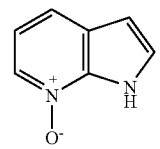

A solution of 1H-pyrrolo[2,3-b]pyridine (1a)

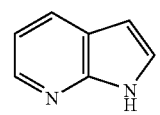

(2.973 kg) in ethyl acetate (22.562 kg) was cooled to 0 to 5° C. To the cooled solution was added a solution of mCPBA (6.872 kg, 1.22 eq) in ethyl acetate (14.884 kg) over the course of about 1.5 h. The residual mCPBA was washed into the reaction mixture by an additional portion of ethyl acetate (5.933 kg). The resulting solution was warmed to 16 to 24° C., and allowed to stir at this temperature until the starting azaindole 1a had been consumed (as judged by reversed phase HPLC analysis). The reaction mixture was then cooled to 0 to 10° C. The resulting slurry was filtered to collect the N-oxide as the meta-chlorobenzoic acid (m-CBA) addition salt 2a'.

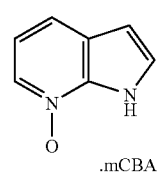

The solid was washed with additional ethyl acetate and then dried to provide 5.716 kg (78.2%) of 2a'.

The mCBA salt 2a' was treated with aqueous base to liberate the N-oxide 2a by the following procedure. A slurry of 2a' (3.338 kg) in deionized water (14.105 kg) at 15 to 25° C. was treated with a sufficient amount of an aqueous solution containing 30% by weight $K_2CO_3$ to raise the pH of the slurry to about 9.5 to 10.5. Additional water (6.441 kg) was added to the mixture, and the temperature maintained at 15 to 25° C. for 1 to 2 h. The slurry was cooled to 0 to 5° C. for 1 to 5 h, and then filtered to recover the precipitate. The precipitate was washed with additional water. The precipitate was then dried to afford 1.258 kg of 2a.

EXAMPLE 2

Preparation of 4-Chloro-1H-pyrrolo[2,3-b]pyridine 3a

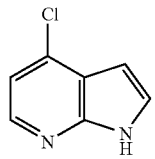

3a

A solution of 2a (1.926 kg) in DMF (9.705 kg) was heated to about 50° C. Methanesulfonyl chloride (4.399 kg) was added to the heated solution at such a rate as to maintain the reaction temperature at 65 to 75° C. The resulting mixture was heated at about 68 to 77° C. until the reaction was judged complete by reversed phase HPLC analysis. The reaction mixture was cooled to about 30° C., and then quenched with water (31.024 kg). Upon cooling the quenched reaction mixture to 5° C., sufficient 10 N NaOH solution was added to raise the pH of the solution to about 7. The resulting slurry was warmed to 25° C., agitated for approximately 1 h, and then filtered to collect the product. The product was washed with additional water, and dried under high vacuum at 45 to 50° C. to afford 1.904 kg of 3a.

EXAMPLE 3

Preparation of 4-Methoxy-1H-pyrrolo[2,3-b]pyridine

4a

A flask equipped with a mechanical stirrer, temperature probe, condenser and Dean-Stark trap was charged with toluene (4.35 L), 3a (217.4 g) and diatomaceous earth (Celite®, 326.1 g). Solid potassium methoxide was added and the resulting suspension was heated. Methanol was collected in the Dean-Stark trap over the course of 1 h. The reaction mixture was then heated at reflux for about 27–29 h. The reaction mixture was cooled to about 80° C. and then water (4.022 L) was added. The suspension was cooled to about 20° C., and then the diatomaceous earth (containing the adsorbed product) was collected by filtration. The filter cake was washed with water (2×217 mL) and then suctioned dry. The resulting filter cake was triturated with $CH_2Cl_2$ (8.68 L) for 30 min. The mixture was filtered and the filter cake was triturated with additional $CH_2Cl_2$ (2×2.1 L). The $CH_2Cl_2$ extracts were combined and evaporated to dryness. The resulting concentrate was azeotroped with ethyl acetate (2×650 mL) to dryness. The concentrate was then triturated with ethyl acetate (650 mL) at about 60° C. and then cooled to 0 to 5° C. The resulting slurry was stirred for 1 h, and then filtered to collect the product. The product was washed with additional cold ethyl acetate (105 mL) and dried at 35° C. to provide 135.2 g of 4a.

EXAMPLE 4

Alternative Preparation of 4-Methoxy-1H-pyrrolo[2,3-b]pyridine

A suspension of 3a (50 g, 0.32770 moles), potassium methoxide (91.94 g, 4.0 equivalents, 1.31079 moles), lithium methoxide (24.89 g, 2.0 equivalents, 0.65539 moles) in a mixture of xylene (300 mL) and t-butanol (37.5 mL) was heated at 116 to 117° C. for about 36 to 40 h. The reaction mixture was cooled to 40–50° C., and then water (826 mL) was slowly introduced. The resulting mixture was cooled to below 10° C. Sufficient concentrated HCl was added to raise the pH of the mixture to 1.5 to 2.0, while maintaining the temperature of the mixture below 20° C. during the addition. The phases were separated. The aqueous layer (containing product) was washed with xylene (2×100 mL) to remove any residual starting material. Sufficient 10 N NaOH was added to raise the pH of the aqueous layer to 6.5–7.0. The resulting beige-colored slurry was stirred at 5–10° C. for about 30 min. The product was collected by filtration. The product was washed with cold water (260 mL) and then heptane (240 mL). The product was dried at 55° C. in vacuo (25–30 in of mercury) to provide 32.5 g (66.7 M %) of 4a.

In certain embodiments it may be preferable to recrystallize the product 4a to provide a more purified product. The following procedure exemplifies recrystallizations that could be performed to purify 4a.

A slurry of crude 4a (34 g) in a mixture of n-butyl acetate (1.19 L) and water (340 mL) was heated to 50° C. to effect dissolution of the solids. The resulting biphasic solution was cooled to 40° C. and the aqueous layer was separated. The n-butyl acetate layer was concentrated to obtain a concentration of about 1 g crude 4a/10 mL mixture. The resulting slurry was heated to 105° C. until all solids had dissolved, and then it was cooled to 40° C. over the course of 15 h. The slurry was then cooled to 0° C. over the course of 2 h. The product was collected by filtration, washed with cold n-butyl acetate (60 mL) and then n-heptane (120 mL). The product was dried at 45–50° C. to provide 29 g (85 M %).

EXAMPLE 5

Preparation of Methyl (4-methoxy-7-azaindol-3-yl)-oxoacetate

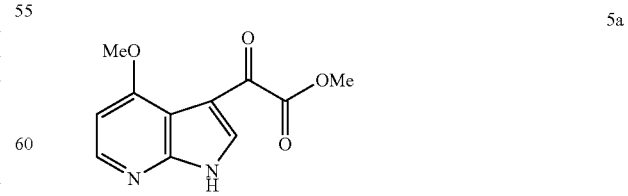

5a

A mixture of 4a (131.17 g, 0.885 mole) and $AlCl_3$ (590.3 g, 4.427 mole) in $CH_2Cl_2$ (3935 mL) was cooled to 0 to 5° C. Nitromethane (918 mL) was added dropwise via addition funnel while maintaining the temperature of the mixture below 12° C. during the course of the addition. Methyl chlorooxoacetate (203.5 mL, 2.213 moles) was then added dropwise via addition funnel while maintaining the temperature of the mixture below 12° C. during the course of the addition. The reaction mixture was stirred while being chilled by an ice bath for a total of 3 h. A chilled (0 to 5° C.) 2.5 M NH$_4$OAc solution was then added dropwise by addition funnel to the reaction mixture while maintaining the temperature of the reaction mixture below 30° C. The biphasic mixture was separated. The aqueous phase was extracted with additional CH$_2$Cl$_2$ (2×1 L). The organic layers were combined and washed with water (1×1.5 L). The organic phase was concentrated on a rotary evaporator to a volume of 2 L. Isopropyl alcohol (2.7 L) was added to the concentrate, and the resulting mixture was concentrated on the rotary evaporator to a volume of 2 L. The coevaporation procedure was repeated with an additional 2.7 L of isopropyl alcohol. The resulting slurry was stirred for 16 h at room temperature. The product was collected by filtration. The filter cake was washed with additional isopropyl alcohol (2×100 mL), and dried to provide crude 5a (169.70 g). By $^1$H NMR analysis the crude product was 4–5/1 ratio of 5a and the corresponding N-1 acetate thereof. The crude product was used without further purification in the next step.

EXAMPLE 6

Preparation of (4-methoxy-7-azaindol-3-yl)-oxoacetic acid

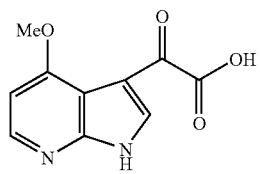

6a 5a (223.7 g, 0.955 mole) was added to a 4N NaOH solution (1190 mL), and the resulting mixture was stirred at 20 to 25° C. for 1 h. The reaction mixture was filtered to remove a very fine, red-colored solid. The resulting filtrate was cooled and 1N HCl (3800 mL) was added. The addition was conducted at such a rate as to keep the reaction temperature at or below 25° C. The resulting mixture was stirred about 30 min and an additional portion (600 mL) of 1 N HCl was added to effect a final pH of 4.5 for the mixture. The resulting slurry was stirred for an additional 30 min. The product was collected by filtration, washed with water (1×800 mL), and then acetone (2×400 mL). The product was dried to yield 6a (195.6 g). The product 6a can be recrystallized from dimethylsulfoxide and water if further purification is desired.

EXAMPLE 7

Preparation of (R)-N-(benzoyl)-3-methyl-N'-[(4-methoxy-7-azaindol-3-yl)-oxoacetyl]-piperazine 7a

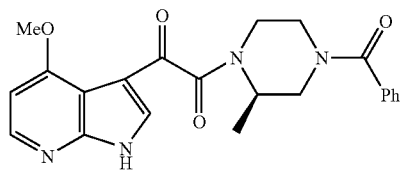

7a

A solution of (chloromethylene)dimethyl ammonium chloride (Vilsmeier reagent, 19.20 g, 0.15 mole) in acetonitrile (600 mL) was prepared. 6a (22.02 g, 0.10 mole) was added to the reaction mixture along with additional acetonitrile (25 mL). The reaction mixture (a yellow-colored suspension) was stirred for about 1 h to form the acid chloride intermediate.

The suspension was cooled to −40° C., and a solution of 8a (24.5 g, 0.12 mole), diisopropylethylamine (DIPEA, 69.8 mL, 4 equivalents) in ethyl acetate (300 mL) was added dropwise to the suspension. The rate of addition was adjusted to maintain the reaction temperature below 35° C. The cooling bath was removed, and the resulting reaction mixture was stirred at 20–25° C. for approximately 4 h. An aqueous solution of 17 wt. % NaCl (800 mL) was added to the reaction mixture, and the resulting mixture was stirred vigorously for 15–20 min. The phases were separated. The organic phase was washed with aqueous 17 wt. % NaCl solution (2×400 mL). The aqueous layers were combined, and extracted with ethyl acetate (3×220 mL). The organic layers were combined, washed with aqueous 20 wt. % NaHSO$_3$ solution (1×400 mL), and evaporated to dryness. The residue was azeotroped with toluene (2×110 mL) at 50–55° C. to provide 42.17 g of the crude product 7a as a yellow-colored foam.

The product was recrystallized by dissolving the crude product in acetone (190 mL) and water (190 mL) at 55–60° C. The orange solution was polish-filtered through a paper filter, and rinsed with additional acetone/water 1:1 (42 mL). The resulting filtrate was warmed to 40° C., seeded with authentic purified product, and then allowed to cool with stirring at 20–25° C. overnight. The resulting beige suspension was warmed to 40–45° C. and stirred at 20–25° C. for about 24 h. The suspension was then cooled to room temperature, and stirred for 4 h, followed by cooling at 0–5° C. for 1 h. The resulting product was collected by filtration, washed with ice cold acetone/water 1:1 (42 mL) and ice cold acetone (21 mL). The solid was dried at 60–65° C. under high vacuum to provide 25.9 g of 7a.

EXAMPLE 8

Screening of Chlorinating Agents for the Conversion of 2a to 3a

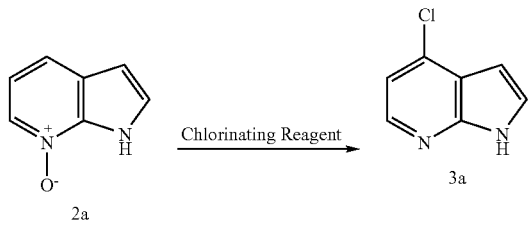

Chlorinating reagents were screened to optimize the ratio of 4-Cl/3-Cl isomers. 100 mg of the N-oxide 2a was utilized in each experiment. Toluene was added to a concentration of 20 mL/g of 2a. The reactions were heated at 110° C. 2.3 Equivalents of chlorinating reagent per mole of 2a were used in each experiment.

Samples of each experiment were assayed by chromatography for the ratio of products. An aliquot from each sample was diluted in CH$_3$CN/H$_2$O (1:1). 5 μL of each diluted sample was injected into the HPLC.

The HPLC used for the assay was equipped with a 3.9×150 mm C-18 column (5 μm, Waters WAT046980 column). The detector was set at λ=230 nm. A gradient elution profile was used:

Solvent A—95% water, 5% CH₃CN, 0.03% trifluoroacetic acid

Solvent B—5% water, 95% CH₃CN, 0.03% trifluoroacetic acid

The gradient was increased from 5% of Solvent B to 95% Solvent B over the course of 25 minutes (End time=20 minutes, post run in 5 minutes). The results are shown in Table 1.

TABLE 1

| Chlorinating Reagent | Starting material 2a | unknown isomer 15 | 3-chloro isomer 12 | 4-chloro isomer 3a | 3,4-dichloro isomer 14 | Ratio (4-Cl/3-Cl) (3a/12) |
|---|---|---|---|---|---|---|
| methanesulfonyl chloride | 43.51 | 6.67 | 6.39 | 39.41 | 4.02 | 7.17 |
| ethanesulfonyl chloride | 83.82 | 2.41 | 1.21 | 10.57 | 2.99 | 9.76 |
| propanesulfonyl 1-chloride | 80.53 | 1.99 | 1.34 | 11.68 | 4.46 | 9.71 |
| 1-butanesulfonyl chloride | 52.92 | 3.93 | 3.16 | 31.36 | 8.63 | 10.91 |
| trifluoromethane sulfonyl chloride | 97.09 | 1.31 | 0.69 | 0.90 | 0.00 | 2.30 |
| benzenesulfonyl chloride | 60.51 | 3.01 | 2.58 | 32.80 | 1.10 | 13.70 |
| p-toluenesulfonyl chloride | 63.03 | 2.70 | 3.06 | 29.89 | 1.31 | 10.76 |
| 4-chlorobenzenesulfonyl chloride | 80.69 | 0.00 | 1.31 | 16.62 | 1.38 | 13.66 |
| 4-methoxy benzenesulfonyl chloride | 65.06 | 2.57 | 3.04 | 28.46 | 0.87 | 10.37 |
| 4-nitro-benzenesulfonyl chloride | 50.17 | 3.87 | 4.20 | 36.09 | 5.67 | 9.60 |
| 2-naphthalenesulfonyl chloride | 76.54 | 0.00 | 0.00 | 22.63 | 0.84 | |
| oxalyl chloride | 95.84 | 1.91 | 1.33 | 0.93 | 0.00 | 1.70 |
| methyl chlorooxoacetate | 68.86 | 3.38 | 5.34 | 10.00 | 12.41 | 2.87 |
| pivaloyl chloride | 72.49 | 17.28 | 5.93 | 1.91 | 2.39 | 1.32 |
| 4-chlorobenzoyl chloride | 26.33 | 38.12 | 12.22 | 6.47 | 16.86 | 1.53 |
| 4-nitrobenzoyl chloride | 27.15 | 36.89 | 9.62 | 6.39 | 19.94 | 1.66 |
| 3-(chloromethyl)-benzoyl chloride | 29.00 | 11.32 | 8.42 | 4.75 | 46.51 | 1.56 |
| methyl choroformate | 97.65 | 0.73 | 0.18 | 0.19 | 1.25 | 2.07 |
| Vilsmeier reagent | 5.95 | 0.46 | 35.59 | 57.12 | 0.87 | 2.61 |
| Rt | 3.11 | 4.83 | 6.93 | 7.37 | 11.52 | |
| RRt | 0.449 | 0.697 | 1.000 | 1.063 | 1.662 | |

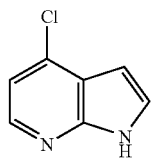

2a unknown   15

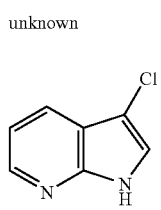

12

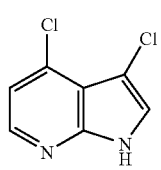

14

As can be seen from Table 1, among the chlorinating agents screened, methanesulfonyl chloride, benzenesulfonyl chloride and p-toluenesulfonyl chloride showed promising results in terms of conversion and 4-Cl/3-Cl ratio.

EXAMPLE 9

Screening of Reaction Solvents for the Conversion of 2a to 3a Using Methanesulfonyl Chloride as a Chlorinating Reagent

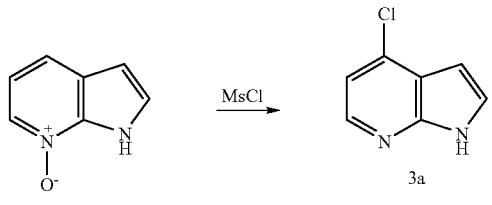

In this experiment, various solvents were screened using methanesulfonyl chloride as the chlorinating reagents. In each experiment 2.5 molar equivalents of methanesulfonyl chloride per mole of 2a (500 mg) were used. The reactions were heated at 70–80° C. for 1.5 h. The concentration was 20 mL of each solvent per gram of 2a. HPLC methods were used to assay the products in the experiments. The HPLC conditions were the same as those used in Example 7. The results are shown in Table 2.

TABLE 2

| Run | Solvent | additive | Rt<br>RRt<br>2a | 2.98<br>0.34<br>unknown<br>15 | 5.39<br>0.62<br>3-Cl<br>12 | 8.14<br>0.94<br>4-Cl<br>3a | 8.66<br>1.00<br>3,4 di-Cl<br>14 | 11.09<br>1.28<br>16 | 12.62<br>1.46<br>Ratio<br>(3a/12) |
|---|---|---|---|---|---|---|---|---|---|
| 1 | Me-THF | none | 42.67 | 6.63 | 5.03 | 26.29 | 13.68 | 5.70 | 6.23 |
| 2 | Me-THF | LiCl<br>(5 eq) | 34.86 | 7.16 | 12.85 | 36.25 | 7.18 | 1.69 | 3.82 |
| 3 | Isobutyl<br>acetate | none | 58.43 | 5.43 | 4.81 | 20.10 | 8.13 | 3.10 | 5.18 |
| 4 | CH$_3$CN | none | 35.88 | 4.73 | 5.06 | 49.17 | 1.64 | 3.53 | 10.72 |
| 5 | Toluene | none | 57.24 | 4.02 | 2.91 | 23.79 | 8.22 | 3.81 | 9.18 |
| 6 | ClCH$_2$CH$_2$Cl | none | 68.01 | 1.53 | 2.97 | 24.12 | 2.13 | 1.24 | 9.12 |

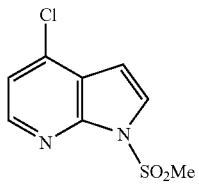

16

From the data presented in Table 2, it was observed that acetonitrile gave superior results in terms of both N-4/N-3 ratio, as well as conversion.

Acetonitrile was then used as the reaction solvent to compare use of methanesulfonyl chloride and p-toluenesulfonyl chloride. In these experiments, 100 mg of 2a was used at a concentration of 20 mL of acetonitrile per gram of 2a. 2.5 equivalents of each chlorinating reagent was used in the experiments. Each experiment was conducted by heating at 70–80° C. for 5 h and 10 min. The results are shown in Table 3.

TABLE 3

| Run | Solvent | Reagent | Rt<br>RRt<br>2a | 2.98<br>0.34<br>unknown<br>15 | 5.39<br>0.62<br>3-Cl<br>12 | 8.14<br>0.94<br>4-Cl<br>3a | 8.66<br>1.00<br>di-Cl<br>14 | 11.09<br>1.28<br>16 | 12.62<br>1.46<br>Ratio<br>(3a/12) |
|---|---|---|---|---|---|---|---|---|---|
| 1 | CH$_3$CN | MeSO$_2$Cl | 12.9 | 7.5 | 7.8 | 66.8 | 2.6 | 2.4 | 9.60 |
| 2 | CH$_3$CN | pTolSO$_2$Cl | 21.5 | 4.9 | 5.8 | 66.8 | 1.1 | | 12.61 |

Examples of such solvents used in the various reactions of this invention are identified in the discussion of the reaction schemes and in the examples.

"Strong base" means a non aqueous base such as sodium-, potassium-, lithium hexamethyldisilazide, lithium diisopropyl amide, and the like.

Abbreviations
DMF N,N-dimethylformamide
THF tetrahydrofuran
MeOH methanol
Ether diethyl ether
DMSO dimethylsulfoxide
EtOAc ethyl acetate
AcOH acetic acid
Ac acetyl
Me methyl
Et ethyl
DEPBT 3-(diethoxyphosphoryloxy)-1,2,3-benzotriazin-4(3H)-one
DIPEA diisopropylethylamine
mCPBA meta-chloroperoxybenzoic acid

Definitions

The following terms shall, for the purposes of this application, have the respective meanings set forth below.

"Alkyl" includes linear and branched alkyl groups, e.g., methyl, ethyl, t-butyl, and the like. Preferred alkyl groups contain 1 to 3 carbon atoms.

"Aryl" alone or in combination shall include both carbocyclic and heterocyclic aromatic compounds.

"Carbocyclic aromatic solvent" shall include substituted benzene compounds. Preferred substituents include alkyl (particularly methyl), chloro, and nitro. Preferred carbocyclic aromatic solvents include toluene, xylene, and mesitylene.

"Inert organic solvent" means any organic solvent or combination of solvents that is unreactive in the reaction being conducted, and is a solvent for the reactants.

mCBA meta-chlorobenzoic acid
pTol paratoluene
azaindole 1H-pyrrolopyridine
7-azaindole 1H-pyrrolo[2,3-b]pyridine Where noted above, publications and references, including but not limited to patents and patent applications, cited in this specification are herein incorporated by reference in their entirety in the entire portion cited as if each individual publication or reference were specifically and individually indicated to be incorporated by reference herein as being fully set forth. Any patent application to which this application claims priority is also incorporated by reference herein in the manner described above for publications and references.

While this invention has been described with an emphasis upon preferred embodiments, it will be obvious to those of ordinary skill in the art that variations in the preferred devices and methods may be used and that it is intended that the invention may be practiced otherwise than as specifically described herein. Accordingly, this invention includes all modifications encompassed within the spirit and scope of the invention as defined by the claims that follow.

What is claimed is:

1. A process for the preparation of a compound of the formula

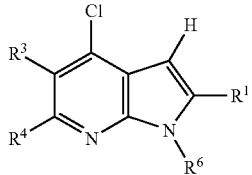

wherein, $R^1$, $R^3$ and $R^4$ are each independently selected from the group of H, $C_1$–$C_6$ alkyl, $C_3$–$C_6$ cycloalkyl, $C_2$–$C_6$ alkenyl, $C_4$–$C_6$ cycloalkenyl, $C_2$–$C_6$ alkynyl, halogen, cyano, phenyl, $C(O)R^5$, $C(O)NR^8R^9$, $OR^{10}$, $SR^{11}$, and $NR^{12}R^{13}$;

$R^5$ is independently selected from the group consisting of H, $C_1$–$C_6$ alkyl, $C_3$–$C_6$ cycloalkyl, $C_2$–$C_6$ alkenyl, and $C_4$–$C_6$ cycloalkenyl;

$R^8$ and $R^9$ are each independently selected from the group consisting of $C_1$–$C_6$ alkyl, $C_3$–$C_6$ cycloalkyl, $C_3$–$C_6$ alkenyl, $C_4$–$C_6$ cycloalkenyl and $C_3$–$C_6$ alkynyl; provided the carbon atoms which comprise the carbon-carbon double bond of said $C_3$–$C_6$ alkenyl or the carbon-carbon triple bond of said $C_3$–$C_6$ alkynyl are not the point of attachment to the nitrogen to which $R^8$ or $R^9$ is attached;

$R^{10}$ and $R^{11}$ are each independently selected from the group consisting of $C_1$–$C_6$ alkyl, $C_1$–$C_6$ alkyl substituted with one to three halogen atoms, $C_3$–$C_6$ cycloalkyl, $C_2$–$C_6$ alkenyl, $C_4$–$C_6$ cycloalkenyl and $C_3$–$C_6$ alkynyl; provided the carbon atoms which comprise said carbon-carbon triple bond of said $C_3$–$C_6$ alkynyl are not the point of attachment to the oxygen or sulfur to which $R^{10}$ or $R^{11}$ is attached;

$R^{12}$ and $R^{13}$ are each independently selected from the group consisting of H, $C_1$–$C_6$ alkyl, $C_3$–$C_6$ cycloalkyl, $C_3$–$C_6$ alkenyl, $C_4$–$C_6$ cycloalkenyl and $C_3$–$C_6$ alkynyl; and $C(O)R^{14}$; provided the carbon atoms which comprise the carbon-carbon double bond of said $C_3$–$C_6$ alkenyl, $C_4$–$C_6$ cycloalkenyl or the carbon-carbon triple bond of said $C_3$–$C_6$ alkynyl are not the point of attachment to the nitrogen to which $R^{12}$ or $R^{13}$ is attached;

$R^{14}$ is selected from the group consisting of H, $C_1$–$C_6$ alkyl, $C_3$–$C_6$ cycloalkyl, $C_2$–$C_6$ alkenyl, $C_4$–$C_6$ cycloalkenyl and $C_2$–$C_6$ alkynyl;

$R^6$ is selected from the group consisting of H, $C_1$–$C_6$ alkyl, $C_3$–$C_6$ cycloalkyl, $C_4$–$C_6$ cycloalkenyl, $C(O)NR^{16}R^{17}$, benzyl, $C_3$–$C_6$ alkenyl and $C_3$–$C_6$ alkynyl; provided the carbon atoms which comprise the carbon-carbon double bond of said $C_3$–$C_6$ alkenyl or the carbon-carbon triple bond of said $C_3$–$C_6$ alkynyl are not the point of attachment to the nitrogen to which $R^6$ is attached;

$R^{16}$ and $R^{17}$ are each independently selected from the group consisting of H, $C_1$–$C_6$ alkyl, $C_3$–$C_6$ cycloalkyl, $C_3$–$C_6$ alkenyl, $C_5$–$C_6$ cycloalkenyl and $C_3$–$C_6$ alkynyl; provided the carbon atoms which comprise the carbon-carbon double bond of said $C_3$–$C_6$ alkenyl, $C_5$–$C_6$ cycloalkenyl or the carbon-carbon triple bond of the $C_3$–$C_6$ alkynyl are not the point of attachment to the nitrogen to which $R^{16}$ and $R^{17}$ are attached;

the process comprising: chlorinating a compound of the formula

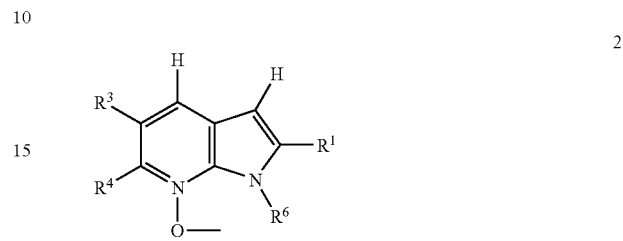

with a chlorinating agent selected from one of (a) a compound of the formula

wherein $R^a$ is $C_1$–$C_4$ alkyl; trifluoromethyl; phenyl or naphthalene, which phenyl or napthalene can be substituted with one or more H, $C_1$–$C_6$ alkyl, $C_3$–$C_6$ cycloalkyl, $C_2$–$C_6$ alkenyl, $C_4$–$C_6$ cycloalkenyl, $C_2$–$C_6$ alkynyl, halogen, cyano, nitro, phenyl, $C(O)R^5$, $C(O)NR^8R^9$, $OR^{10}$;

(b) a compound of the formula

wherein $R^b$ is $C_1$–$C_4$ alkyl; trihalomethyl; $C(O)R^5$; phenyl or naphthalene, which phenyl or naphthalene can be substituted with one or more H, $C_1$–$C_6$ alkyl, $C_3$–$C_6$ cycloalkyl, $C_2$–$C_6$ alkenyl, $C_4$–$C_6$ cycloalkenyl, $C_2$–$C_6$ alkynyl, halogen, cyano, nitro, phenyl, $C(O)R^5$, $C(O)NR^8R^9$, $OR^{10}$; or (c) a compound of the formula

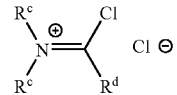

wherein $R^c$ is independently $C_1$–$C_4$ alkyl; trifluoromethyl; phenyl or naphthalene, which naphthalene is substituted with one or more H, $C_1$–$C_6$ alkyl, $C_3$–$C_6$ cycloalkyl, $C_2$–$C_6$ alkenyl, $C_4$–$C_6$ cycloalkenyl, $C_2$–$C_6$ alkynyl, halogen, cyano, phenyl and $OR^{10}$; and wherein $R^d$ is H, $C_1$–$C_4$ alkyl; halogen; trifluoromethyl; phenyl or naphthalene, which naphthalene is substituted with one or more H, $C_1$–$C_6$ alkyl, $C_3$–$C_6$ cycloalkyl, $C_2$–$C_6$ alkenyl, $C_4$–$C_6$ cycloalkenyl, $C_2$–$C_6$ alkynyl, halogen, cyano, phenyl and $OR^{10}$.

2. The process of claim 1, wherein the chlorinating agent is $R^aSO_2Cl$.

3. The process of claim 2, wherein the chlorinating agent is methanesulfonyl chloride.

4. The process of claim 1, wherein the chlorinating is conducted in a polar or dipolar aprotic solvent.

5. The process of claim 3, wherein there is from about 2 to 3 equivalents of methanesulfonyl chloride.

6. The process of claim 1, wherein a concentration of the compound 2 is from about 1 to 2 M.

7. The process of claim 1, wherein the reaction is performed at a temperature of from about 45 to 90° C.

8. The process of claim 1, wherein $R^1$ and $R^3$ are H; $R^4$ is H, halogen or cyano; and $R^6$ is H, methyl or allyl.

9. A process for the preparation of a compound of the formula

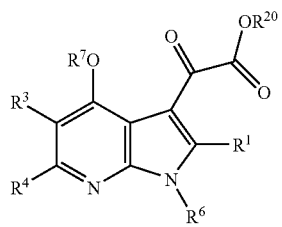

wherein,
- $R^1$, $R^3$ and $R^4$ are each independently selected from the group of H, $C_1-C_6$ alkyl, $C_3-C_6$ cycloalkyl, $C_2-C_6$ alkenyl, $C_4-C_6$ cycloalkenyl, $C_2-C_6$ alkynyl, halogen, cyano, phenyl, $C(O)R^5$, $C(O)NR^8R^9$, $OR^{10}$, $SR^{11}$, and $NR^{12}R^{13}$;
- $R^5$ is independently selected from the group consisting of H, $C_1-C_6$ alkyl, $C_3-C_6$ cycloalkyl, $C_2-C_6$ alkenyl, and $C_4-C_6$ cycloalkenyl;
- $R^8$ and $R^9$ are each independently selected from the group consisting of $C_1-C_6$ alkyl, $C_3-C_6$ cycloalkyl, $C_3-C_6$ alkenyl, $C_4-C_6$ cycloalkenyl and $C_3-C_6$ alkynyl; provided the carbon atoms which comprise the carbon-carbon double bond of said $C_3-C_6$ alkenyl or the carbon-carbon triple bond of said $C_3-C_6$ alkynyl are not the point of attachment to the nitrogen to which $R^8$ or $R^9$ is attached;
- $R^{10}$ and $R^{11}$ are each independently selected from the group consisting of $C_1-C_6$ alkyl, $C_1-C_6$ alkyl substituted with one to three halogen atoms, $C_3-C_6$ cycloalkyl, $C_2-C_6$ alkenyl, $C_4-C_6$ cycloalkenyl and $C_3-C_6$ alkynyl; provided the carbon atoms which comprise said carbon-carbon triple bond of said $C_3-C_6$ alkynyl are not the point of attachment to the oxygen or sulfur to which $R^{10}$ or $R^{11}$ is attached;
- $R^{12}$ and $R^{13}$ are each independently selected from the group consisting of H, $C_1-C_6$ alkyl, $C_3-C_6$ cycloalkyl, $C_3-C_6$ alkenyl, $C_4-C_6$ cycloalkenyl and $C_3-C_6$ alkynyl; and $C(O)R^{14}$; provided the carbon atoms which comprise the carbon-carbon double bond of said $C_3-C_6$ alkenyl, $C_4-C_6$ cycloalkenyl or the carbon-carbon triple bond of said $C_3-C_6$ alkynyl are not the point of attachment to the nitrogen to which $R^{12}$ or $R^{13}$ is attached;
- $R^{14}$ is selected from the group consisting of H, $C_1-C_6$ alkyl, $C_3-C_6$ cycloalkyl, $C_2-C_6$ alkenyl, $C_4-C_6$ cycloalkenyl and $C_2-C_6$ alkynyl;
- $R^6$ is selected from the group consisting of H, $C_1-C_6$ alkyl, $C_3-C_6$ cycloalkyl, $C_4-C_6$ cycloalkenyl, $C(O)NR^{16}R^{17}$, benzyl, $C_3-C_6$ alkenyl and $C_3-C_6$ alkynyl; provided the carbon atoms which comprise the carbon-carbon double bond of said $C_3-C_6$ alkenyl or the carbon-carbon triple bond of said $C_3-C_6$ alkynyl are not the point of attachment to the nitrogen to which $R^6$ is attached;
- $R^{16}$ and $R^{17}$ are each independently selected from the group consisting of H, $C_1-C_6$ alkyl, $C_3-C_6$ cycloalkyl, $C_3-C_6$ alkenyl, $C_5-C_6$ cycloalkenyl and $C_3-C_6$ alkynyl; provided the carbon atoms which comprise the carbon-carbon double bond of said $C_3-C_6$ alkenyl, $C_5-C_6$ cycloalkenyl or the carbon-carbon triple bond of the $C_3-C_6$ alkynyl are not the point of attachment to the nitrogen to which $R^{16}$ and $R^{17}$ are attached;
- $R^7$ is selected from the group consisting of $CH_3$, $CH_2CH_3$, $CH_2CF_3$ and $CH_2CH_2CH_3$; and
- $R^{20}$ is selected from the group consisting of $C_1-C_6$ alkyl, $C_3-C_6$ cycloalkyl, aryl[$C_1-C_6$]alkyl, and aryl;

the process comprising: reacting a compound of the formula

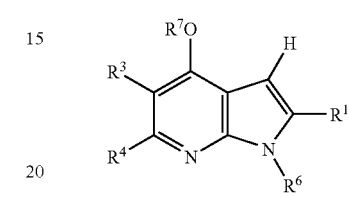

with a chlorooxoacetate reagent of the formula

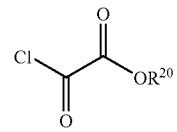

in the presence of a Lewis acid.

10. The process of claim 9, wherein the Lewis acid is aluminum trichloride present in an amount of at least four equivalents.

11. The process of claim 9, wherein the reaction is conducted in a solvent of dichloromethane:[$C_1-C_3$]nitroalkane in about a 4:1 to 17:3 ratio.

12. A process for the preparation of a compound of the formula

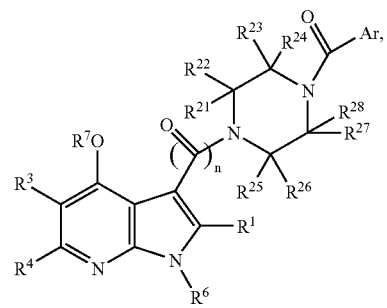

wherein
- $R^1$, $R^3$ and $R^4$ are each independently selected from the group of H, $C_1-C_6$ alkyl, $C_3-C_6$ cycloalkyl, $C_2-C_6$ alkenyl, $C_4-C_6$ cycloalkenyl, $C_2-C_6$ alkynyl, halogen, cyano, phenyl, $C(O)R^5$, $C(O)NR^8R^9$, $OR^{10}$, $SR^{11}$, and $NR^{12}R^{13}$;
- $R^5$ is independently selected from the group consisting of H, $C_1-C_6$ alkyl, $C_3-C_6$ cycloalkyl, $C_2-C_6$ alkenyl, and $C_4-C_6$ cycloalkenyl;
- $R^8$ and $R^9$ are each independently selected from the group consisting of $C_1-C_6$ alkyl, $C_3-C_6$ cycloalkyl, $C_3-C_6$ alkenyl, $C_4$–$C_6$ cycloalkenyl and $C_3$–$C_6$ alkynyl; provided the carbon atoms which comprise the carbon-carbon double bond of said $C_3$–$C_6$ alkenyl or the carbon-carbon triple bond of said $C_3$–$C_6$ alkynyl are not the point of attachment to the nitrogen to which $R^8$ or $R^9$ is attached;

$R^{10}$ and $R^{11}$ are each independently selected from the group consisting of $C_1$–$C_6$ alkyl, $C_1$–$C_6$ alkyl substituted with one to three halogen atoms, $C_3$–$C_6$ cycloalkyl, $C_2$–$C_6$ alkenyl, $C_4$–$C_6$ cycloalkenyl and $C_3$–$C_6$ alkynyl; provided the carbon atoms which comprise said carbon-carbon triple bond of said $C_3$–$C_6$ alkynyl are not the point of attachment to the oxygen or sulfur to which $R^{10}$ or $R^{11}$ is attached;

$R^{12}$ and $R^{13}$ are each independently selected from the group consisting of $C_1$–$C_6$ alkyl, $C_3$–$C_6$ cycloalkyl, $C_3$–$C_6$ alkenyl, $C_4$–$C_6$ cycloalkenyl and $C_3$–$C_6$ alkynyl; and $C(O)R^{14}$; provided the carbon atoms which comprise the carbon-carbon double bond of said $C_3$–$C_6$ alkenyl, $C_4$–$C_6$ cycloalkenyl or the carbon-carbon triple bond of said $C_3$–$C_6$ alkynyl are not the point of attachment to the nitrogen to which $R^{12}$ or $R^{13}$ is attached;

$R^{14}$ is selected from the group consisting of H, $C_1$–$C_6$ alkyl, $C_3$–$C_6$ cycloalkyl, $C_2$–$C_6$ alkenyl, $C_4$–$C_6$ cycloalkenyl and $C_2$–$C_6$ alkynyl;

$R^6$ is selected from the group consisting of H, $C_1$–$C_6$ alkyl, $C_3$–$C_6$ cycloalkyl, $C_4$–$C_6$ cycloalkenyl, $C(O)NR^{16}R^{17}$, benzyl, $C_3$–$C_6$ alkenyl and $C_3$–$C_6$ alkynyl; provided the carbon atoms which comprise the carbon-carbon double bond of said $C_3$–$C_6$ alkenyl or the carbon-carbon triple bond of said $C_3$–$C_6$ alkynyl are not the point of attachment to the nitrogen to which $R^6$ is attached;

$R^{16}$ and $R^{17}$ are each independently selected from the group consisting of H, $C_1$–$C_6$ alkyl, $C_3$–$C_6$ cycloalkyl, $C_3$–$C_6$ alkenyl, $C_5$–$C_6$ cycloalkenyl and $C_3$–$C_6$ alkynyl; provided the carbon atoms which comprise the carbon-carbon double bond of said $C_3$–$C_6$ alkenyl, $C_5$–$C_6$ cycloalkenyl or the carbon-carbon triple bond of the $C_3$–$C_6$ alkynyl are not the point of attachment to the nitrogen to which $R^{16}$ and $R^{17}$ are attached;

$R^7$ is selected from the group consisting of $CH_3$, $CH_2CH_3$, $CH_2CF_3$ and $CH_2CH_2CH_3$;

$R^{21}$, $R^{22}$, $R^{23}$, $R^{24}$, $R^{25}$, $R^{26}$, $R^{27}$ and $R^{28}$ are each independently selected from the group consisting of H, $C_1$–$C_6$ alkyl, $C_3$–$C_6$ cycloalkyl, $C_2$–$C_6$ alkenyl, $C_4$–$C_6$ cycloalkenyl, $C_2$–$C_6$ alkynyl, $CR^{29}R^{30}OR^{31}$, $C(O)R^{32}$, $CR^{33}(OR^{34})OR^{35}$, $CR^{36}NR^{37}R^{38}$, $C(O)OR^{39}$, $C(O)NR^{40}R^{41}$, $CR^{42}R^{43}F$, $CR^{44}F_2$, and $CF_3$;

$R^{29}$, $R^{30}$, $R^{31}$, $R^{32}$, $R^{33}$, $R^{36}$, $R^{42}$, $R^{43}$ and $R^{44}$ are each independently selected from the group consisting of H, $C_1$–$C_6$ alkyl, $C_3$–$C_6$ cycloalkyl, $C_2$–$C_6$ alkenyl, $C_4$–$C_6$ cycloalkenyl, $C_2$–$C_6$ alkynyl and $C(O)R^{45}$;

$R^{34}$, $R^{35}$ and $R^{39}$ are each independently selected from the group consisting of H, $C_1$–$C_6$ alkyl, $C_3$–$C_6$ cycloalkyl, $C_3$–$C_6$ alkenyl, $C_4$–$C_6$ cycloalkenyl, and $C_3$–$C_6$ alkynyl; provided the carbon atoms which comprise the carbon-carbon triple bond of said $C_3$–$C_6$ alkynyl are not the point of attachment to the oxygen to which $R^{35}$ and $R^{39}$ are attached;

$R^{37}$ and $R^{38}$ are each independently selected from the group consisting of H, $C_1$–$C_6$ alkyl, $C_3$–$C_6$ cycloalkyl, $C_3$–$C_6$ alkenyl, $C_4$–$C_6$ cycloalkenyl and $C_3$–$C_6$ alkynyl; provided the carbon atoms which comprise the carbon-carbon triple bond of said $C_3$–$C_6$ alkynyl are not the point of attachment to the nitrogen to which $R^{37}$ and $R^{38}$ are attached;

$R^{40}$ and $R^{41}$ are each independently selected from the group consisting of H, $C_1$–$C_6$ alkyl, $C_3$–$C_6$ cycloalkyl, $C_2$–$C_6$ alkenyl, $C_4$–$C_6$ cycloalkenyl and $C_3$–$C_6$ alkynyl; provided the carbon atoms which comprise the carbon-carbon triple bond of said $C_3$–$C_6$ alkynyl are not the point of attachment to the nitrogen to which $R^{40}$ and $R^{41}$ are attached;

$R^{45}$ is selected from the group consisting of H, $C_1$–$C_6$ alkyl, $C_3$–$C_6$ cycloalkyl, $C_2$–$C_6$ alkenyl, $C_4$–$C_6$ cycloalkenyl, and $C_2$–$C_6$ alkynyl;

Ar is selected from the group consisting of

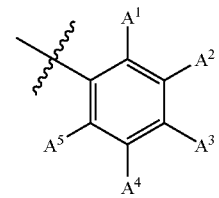 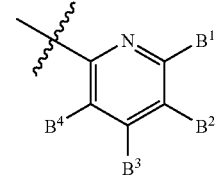

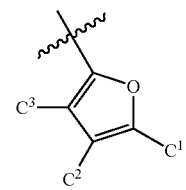 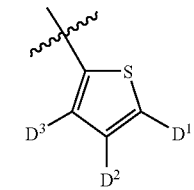

$A^1$, $A^2$, $A^3$, $A^4$, $A^5$, $B^1$, $B^2$, $B^3$, $B^4$, $C^1$, $C^2$, $C^3$, $D^1$, $D^2$ and $D^3$ are each selected from the group consisting of H, cyano, halogen, nitro, $C_1$–$C_6$ alkyl, $C_3$–$C_6$ cycloalkyl, $C_2$–$C_6$ alkenyl, $C_4$–$C_6$ cycloalkenyl, $C_2$–$C_6$ alkynyl, $OR^{46}$, $NR^{47}R^{48}$, $SR^{49}$, $N_3$ and $CH(-N=N-)-CF_3$;

$R^{46}$ is selected from the group consisting of H, $C_1$–$C_6$ alkyl, $C_3$–$C_6$ cycloalkyl, $C_2$–$C_6$ alkenyl, $C_4$–$C_6$ cycloalkenyl, $C_2$–$C_6$ alkynyl; provided the carbon atoms which comprise the carbon-carbon triple bond of said $C_3$–$C_6$ alkynyl are not the point of attachment to the nitrogen to which $R^{46}$ is attached;

$R^{47}$ and $R^{48}$ are each independently selected from the group consisting of H, $C_1$–$C_6$ alkyl, $C_3$–$C_6$ cycloalkyl, $C_3$–$C_6$ alkenyl, $C_5$–$C_6$ cycloalkenyl, $C_3$–$C_6$ alkynyl, and $C(O)R^{51}$; provided the carbon atoms which comprise the carbon-carbon double bond of said $C_5$–$C_6$ alkenyl, $C_4$–$C_6$ cycloalkenyl, or the carbon-carbon triple bond of said $C_3$–$C_6$ alkynyl are not the point of attachment to the nitrogen to which $R^{47}$ and $R^{48}$ are attached;

$R^{49}$ is selected from the group consisting of H, $C_1$–$C_6$ alkyl, $C_3$–$C_6$ cycloalkyl, $C_2$–$C_6$ alkenyl, $C_4$–$C_6$ cycloalkenyl, $C_3$–$C_6$ alkynyl and $C(O)R^{50}$; provided the carbon atoms which comprise the carbon-carbon triple bond of said $C_3$–$C_6$ alkynyl are not the point of attachment to the sulfur to which $R^{47}$ is attached;

$R^{50}$ is $C_1$–$C_6$ alkyl or $C_3$–$C_6$ cycloalkyl; and $R^{51}$ is selected from the group consisting of H, $C_1$–$C_6$ alkyl and $C_3$–$C_6$ cycloalkyl;

the process comprising:
(a) treating a compound of the formula

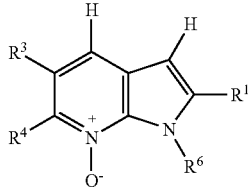

with a chlorinating agent selected from one of a sulfonyl chloride reagent of the formula

wherein $R^a$ is $C_1$–$C_4$ alkyl; trifluoromethyl; phenyl or naphthalene, which phenyl or napthalene can be substituted with one or more H, $C_1$–$C_6$ alkyl, $C_3$–$C_6$ cycloalkyl, $C_2$–$C_6$ alkenyl, $C_4$–$C_6$ cycloalkenyl, $C_2$–$C_6$ alkynyl, halogen, cyano, nitro, phenyl, $C(O)R^5$, $C(O)NR^8R^9$, $OR^{10}$;

(ii) a compound of the formula

wherein $R^b$ is $C_1$–$C_4$ alkyl; trihalomethyl; $C(O)R^5$; phenyl or naphthalene, which phenyl or naphthalene can be substituted with one or more H, $C_1$–$C_6$ alkyl, $C_3$–$C_6$ cycloalkyl, $C_2$–$C_6$ alkenyl, $C_4$–$C_6$ cycloalkenyl, $C_2$–$C_6$ alkynyl, halogen, cyano, nitro, phenyl, $C(O)R^5$, $C(O)NR^8R^9$, $OR^{10}$; or (iii) a compound of the formula

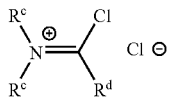

wherein $R^c$ is independently H, $C_1$–$C_4$ alkyl; trifluoromethyl; phenyl or naphthalene, which naphthalene is substituted with one or more H, $C_1$–$C_6$ alkyl, $C_3$–$C_6$ cycloalkyl, $C_2$–$C_6$ alkenyl, $C_4$–$C_6$ cycloalkenyl, $C_2$–$C_6$ alkynyl, halogen, cyano, phenyl and $OR^{10}$; and wherein $R^d$ is H, $C_1$–$C_4$ alkyl; halogen; trifluoromethyl; phenyl or naphthalene, which naphthalene is substituted with one or more H, $C_1$–$C_6$ alkyl, $C_3$–$C_6$ cycloalkyl, $C_2$–$C_6$ alkenyl, $C_4$–$C_6$ cycloalkenyl, $C_2$–$C_6$ alkynyl, halogen, cyano, phenyl and $OR^{10}$;

to give a compound of the formula

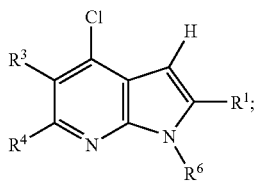

3

(b) reacting the compound of the formula 3 with a potassium alkoxide of the formula

to give a compound of the formula

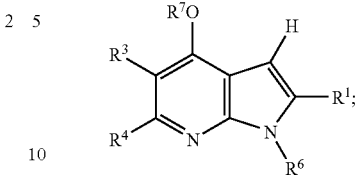

4

(c) treating the compound of the formula 4 with a compound of the formula

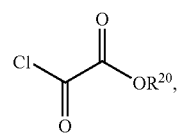

9 wherein $R^{20}$ is alkyl, cycloalkyl, arylalkyl or aryl, in the presence of a Lewis acid to give a compound of the formula

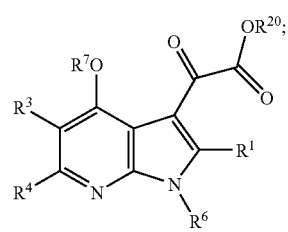

5

(d) hydrolyzing the ester of the compound of the formula 5 to give a compound of the formula

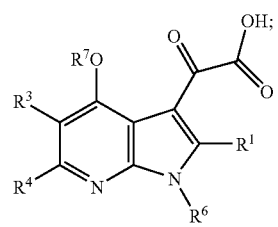

6

(e) coupling the compound of the formula 6 with a compound of the formula

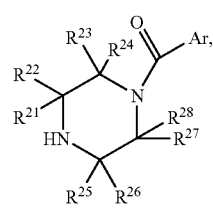

8 using an acyl activating reagent to give the compound of the formula 7.

13. The process of claim 12, wherein the chlorination of step (a) comprises treatment with about 2 to 3 equivalents of methanesulfonyl in a polar aprotic solvent at a temperature of about 45 to 90° C.

14. The process of claim 12, wherein the Lewis acid in step (c) is aluminum trichloride.

15. The process of claim 12, wherein in step (c), the compound of the formula 9 is methyl chlorooxoacetate.

16. The process of claim 12, wherein the acyl activating agent in step (e) is selected from the group consisting of Vilsmeier reagent and oxalyl chloride.

17. The process of claim 12, wherein the coupling of step (e) comprises:
  (i) treating the compound of the formula 6 with Vilsmeier reagent; and
  (ii) treating the product from step (i) with the compound of the formula 8.

18. The process of claim 12, wherein the compound of the formula 2 is prepared by a process comprising: oxidizing a compound of the formula

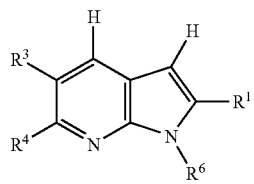

1 with an oxidizing agent to give the compound of the formula 2, or a salt thereof.

19. The process of the claim 18, wherein the oxidizing agent in the oxidation of step (a) is selected from the group consisting of m-chloroperoxybenzoic acid, hydrogen peroxide, peracetic acid, hydrogen peroxide-urea reagent, magnesium monoperoxyphthalate hexahydrate, and oxone.

20. The process of claim 19, wherein the oxidizing agent is m-chloroperoxybenzoic acid.

21. The process of claim 20, wherein the oxidation of step (a) comprises treatment with from about 1 to 3 equivalents of meta-chloroperoxybenzoic acid in ethyl acetate.

22. The process of claim 12, wherein $R^7$ is $CH_3O$.

23. The process of claim 22, wherein $R^1$, $R^3$, $R^4$ and $R^6$ are H.

24. The process of claim 23, wherein the compound of formula 8 in step (e) is

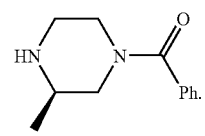

25. A compound of the formula:

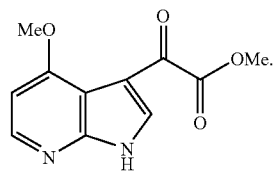

5a

26. A compound of the formula:

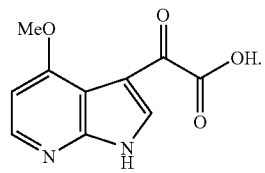

6a

* * * * *

UNITED STATES PATENT AND TRADEMARK OFFICE
CERTIFICATE OF CORRECTION

PATENT NO. : 7,105,677 B2 Page 1 of 1
APPLICATION NO. : 10/948405
DATED : September 12, 2006
INVENTOR(S) : Nachimuthu Soundararajan et al.

It is certified that error appears in the above-identified patent and that said Letters Patent is hereby corrected as shown below:

Title Page,
Item [75], should read:
--[75] Inventors: Nachimuthu Soundararajan, Kendall Park, NJ (US); Serge Benoit, Laval; Stephane Gingras, Montreal, both of Canada--

Signed and Sealed this

Seventeenth Day of April, 2007

JON W. DUDAS
*Director of the United States Patent and Trademark Office*